United States Patent
Tanigawa

(10) Patent No.: US 9,188,665 B2
(45) Date of Patent: Nov. 17, 2015

(54) MEDICAL IMAGE DISPLAY APPARATUS AND METHOD FOR DISPLAYING MEDICAL IMAGES

(75) Inventor: Shunichiro Tanigawa, Tokyo (JP)

(73) Assignee: GE MEDICAL SYSTEMS GLOBAL TECHNOLOGY COMPANY, LLC, Waukesha, WI (US)

( * ) Notice: Subject to any disclaimer, the term of this patent is extended or adjusted under 35 U.S.C. 154(b) by 128 days.

(21) Appl. No.: 13/307,509

(22) Filed: Nov. 30, 2011

(65) Prior Publication Data
US 2012/0133663 A1 May 31, 2012

(30) Foreign Application Priority Data
Nov. 30, 2010 (JP) .................. 2010-266394

(51) Int. Cl.
G09G 5/00 (2006.01)
G01S 7/52 (2006.01)
G01R 33/56 (2006.01)
G06T 11/00 (2006.01)
A61B 8/08 (2006.01)
G01R 33/563 (2006.01)

(52) U.S. Cl.
CPC ............. *G01S 7/52074* (2013.01); *A61B 8/485* (2013.01); *G01R 33/5608* (2013.01); *G06T 11/001* (2013.01); *G01R 33/56358* (2013.01); *G01S 7/52042* (2013.01); *G01S 7/52071* (2013.01)

(58) Field of Classification Search
USPC .......................................................... 345/647
See application file for complete search history.

(56) References Cited

U.S. PATENT DOCUMENTS

| 4,757,820 A * | 7/1988 | Itoh .............................. 600/439 |
| 5,524,636 A * | 6/1996 | Sarvazyan et al. ............ 600/587 |
| 7,608,044 B2 | 10/2009 | Tanigawa |
| 2006/0058649 A1* | 3/2006 | Tamano et al. ............... 600/437 |
| 2010/0222667 A1* | 9/2010 | Osman et al. ................. 600/422 |
| 2011/0019894 A1 | 1/2011 | Tanigawa |

(Continued)

FOREIGN PATENT DOCUMENTS

| CN | 101370431 A | 2/2009 |
| JP | 2004283372 | 10/2004 |
| JP | 2005118152 | 5/2005 |

(Continued)

OTHER PUBLICATIONS

Japanese Office Action; Application No. 2010-266394; dated Oct. 22, 2012; pp. 3.

(Continued)

*Primary Examiner* — Stephen R Koziol
*Assistant Examiner* — Sohum Kaji

(57) ABSTRACT

A medical image display apparatus for displaying medical images of a biological tissue includes a physical quantity calculator that calculates a first physical quantity related to elasticity of the biological tissue, and a display image control unit that displays a first elastic image having a display form corresponding to the first physical quantity calculated by the physical quantity calculator and a second elastic image having a display form corresponding to a second physical quantity related to elasticity of the biological tissue calculated by other another medical image display apparatus as the medical images. The display image control unit displays images in which portions having a same elasticity in the biological tissue in a same display form as the first and second elastic images.

17 Claims, 18 Drawing Sheets

(56) References Cited

U.S. PATENT DOCUMENTS

2011/0054314 A1     3/2011    Tanigawa et al.
2011/0216958 A1*   9/2011    Satoh et al. .................. 382/131

FOREIGN PATENT DOCUMENTS

| | | |
|---|---|---|
| JP | 2008086400 A | 4/2008 |
| JP | 2008126079 | 6/2008 |
| WO | 2005006978 A1 | 1/2005 |
| WO | 2005117712 A1 | 12/2005 |

OTHER PUBLICATIONS

Unofficial translation of CN Search Report issued in connection with corresponding CN Application No. 2011104621661 dated Jun. 24, 2014.

* cited by examiner

PHYSICAL QUANTITY DATA

MEDICAL IMAGE DISPLAY APPARATUS AND METHOD FOR DISPLAYING MEDICAL IMAGES

CROSS REFERENCE TO RELATED APPLICATIONS

This application claims the benefit of Japanese Patent Application No. 2010-266394 filed Nov. 30, 2010, which is hereby incorporated by reference in its entirety

BACKGROUND OF THE INVENTION

The present invention relates to a medical image display apparatus for displaying medical images of a biological tissue and a method for displaying medical images. The present invention relates in particular to a medical image display apparatus for displaying elastic images of a biological tissue as the medical images, and a method for displaying medical images.

An ultrasonic image display apparatus which causes elastic images each comprised of a display form corresponding to the elasticity of a biological tissue to be displayed has been disclosed in, for example, Japanese Patent Application Laid-Open No. 2005-118152 or the like. Even as to an MRI (Magnetic Resonance Imaging) system, a system capable of displaying elastic images of a biological tissue has been disclosed in, for example, Japanese Patent Application Laid-Open No. 2004-283372 or the like. Each of an ultrasound elastic image displayed by the ultrasonic image display apparatus and an MRI elastic image displayed by the MRI system is an image comprised of colors corresponding to the elasticity of the biological tissue, for example.

Incidentally, the MRI elastic image is an image wider in range than the ultrasound elastic image. On the other hand, the ultrasound elastic image is generally more excellent in spatial resolution than the MRI elastic image. Thus, as an image diagnosis that takes advantage of the characteristics of both images, there is, for example, a case where it is desired to display the MRI elastic image at an ultrasound image display apparatus, and confirm and diagnose a portion or region considered to be a diseased portion by real-time ultrasound elastic images excellent in spatial resolution after the diseased portion is specified while seeing images of whole organs such as liver, etc. through the MRI elastic image.

Since, however, the MRI elastic image and the ultrasound elastic image are generated using their corresponding color maps by an MRI system and an ultrasonic diagnostic apparatus, portions or regions having the same elasticity in a biological tissue are displayed in mutually different colors at the respective elastic images. Thus, when a second elastic image generated at other medical image display apparatus is displayed at a medical image display apparatus for displaying a first elastic image, portions having the same elasticity can be displayed in the same display form at the first elastic image and the second elastic image. There has thus been a demand for a medical image display apparatus capable of displaying images useful for diagnosis.

BRIEF SUMMARY OF THE INVENTION

The embodiments described herein provide a medical image display apparatus for displaying medical images of a biological tissue. The apparatus includes a physical quantity calculator which calculates a first physical quantity related to elasticity of the biological tissue, and a display image control unit which causes a first elastic image having a display form corresponding to the first physical quantity calculated by the physical quantity calculator and a second elastic image having a display form corresponding to a second physical quantity related to elasticity of the biological tissue calculated by other medical image display apparatus to be displayed as the medical images, wherein the display image control unit causes images in which portions having the same elasticity in the biological tissue are displayed in the same display form, to be displayed as the first and second elastic images.

According to the embodiments described herein, portions having the same elasticity in a biological tissue are represented in the same display form at the first and second images, so that images useful for diagnosis can be displayed.

Further objects and advantages of the present invention will be apparent from the following description of the preferred embodiments of the invention as illustrated in the accompanying drawings.

DETAILED DESCRIPTION OF THE INVENTION

Figure 1:
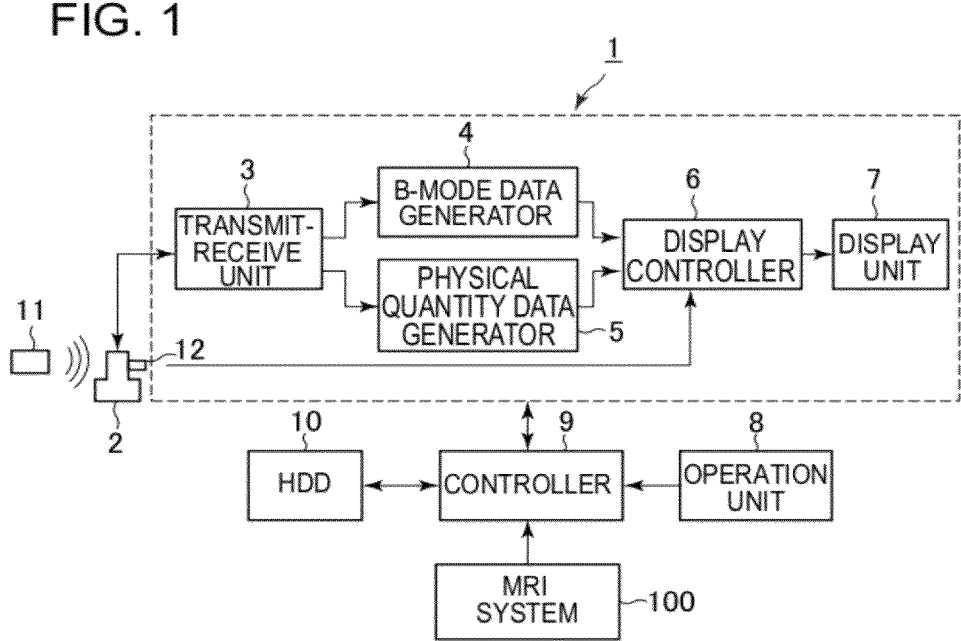
FIG. 1 is a block diagram showing one example of a schematic configuration of an embodiment of an ultrasonic image display apparatus.

Embodiments of the invention will hereinafter be described in detail, based on the accompanying drawings. An ultrasonic image display apparatus 1 shown in FIG. 1 is equipped with an ultrasonic probe 2, a transmit-receive unit 3, a B-mode data generator 4, a physical quantity data generator 5, a display controller 6, a display unit 7, an operation unit 8, a controller 9, a HDD (Hard Disk Drive) 10, a magnetic field generator 11, and a magnetic sensor 12. The ultrasonic image display apparatus 1 is one example illustrative of an embodiment of a medical image display apparatus.

The ultrasonic probe 2 transmits ultrasound to a biological tissue and receives its echoes. An ultrasound elastic image is generated, as will be described later, based on echo signals acquired by performing the transmission/reception of the ultrasound while deforming the biological tissue, by repeating pressure and relaxation in a state in which the ultrasonic probe 2 is being brought into contact with the surface of the biological tissue or adding acoustic radiation pressure from the ultrasonic probe 2.

The ultrasonic probe 2 is equipped with the magnetic sensor 12 including a hole element, for example. Then, the magnetic sensor 12 to detect magnetic field generated from the magnetic field generator 11 includes a magnetic field generating coil. A signal detected by the magnetic sensor 12 is inputted to the display controller 6. The signal detected by the magnetic sensor 12 may be input to the display controller 6 via an unillustrated cable or may be inputted thereto by wireless.

The transmit-receive unit 3 drives the ultrasonic probe 2 under a predetermined scan condition, based on a control signal supplied from the controller 9 to perform the scanning of the ultrasound for every sound ray. The transmit-receive unit 3 performs signal processing such as phasing-adding processing on each echo signal received by the ultrasonic probe 2. The echo signal subjected to the signal processing at the transmit-receive unit 3 is outputted to the B-mode data generator 4 and the physical quantity data generator 5.

The B-mode data generator 4 performs B-mode processing such as logarithmic compression processing, envelop detection processing or the like on the echo signals outputted from the transmit-receive unit 3 to thereby generate B-mode image data. The B-mode data is outputted from the B-mode data generator 4 to the display controller 6.

Figure 2:
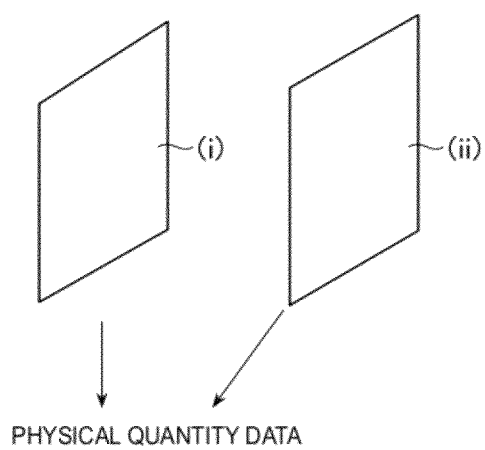
FIG. 2 is a diagram for explaining the generation of physical quantity data.

The physical quantity data generator 5 generates physical quantity data related to the elasticity in the biological tissue, based on the echo signals outputted from the transmit-receive unit 3 (physical quantity data generating function). The physical quantity data generator 5 calculates physical quantities related to the elasticity of the respective regions in the biological tissue, based on two echo signals on the same sound rays that belong to two frames (i) and (ii) different in time as shown in FIG. 2 to thereby generate the physical quantity data (refer to, for example, Japanese Patent Application Laid-Open No. 2008-126079). The physical quantity data generator 5 generates the physical quantity data, targeting within regions of interest R1 and R2 being target for the generation of an ultrasound elastic image UEG to be described later.

The physical quantity data generator 5 calculates a strain S due to the deformation of the biological tissue as the physical quantity. The physical quantity data is data including strains S of the respective regions in the biological tissue. The physical quantity data generator 5 is one example illustrative of an embodiment of a physical quantity data generator. The physical quantity data generating function is one example illustrative of an embodiment of a physical quantity calculating function. Further, the strain S is one example illustrative of an embodiment of a first physical quantity.

Figure 3:
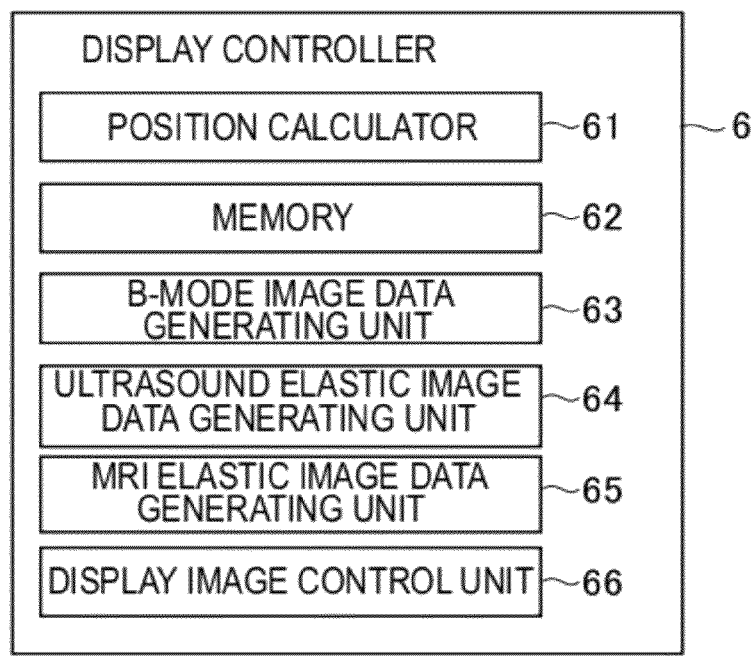
FIG. 3 is a block diagram showing a configuration of a display controller in the ultrasonic image display apparatus shown in FIG. 1.

The B-mode data outputted from the B-mode data generator 4 and the physical quantity data outputted from the physical quantity data generator 5 are inputted to the display controller 6. The display controller 6 has, as shown in FIG. 3, a position calculator 61, a memory 62, a B-mode image data generating unit 63, an ultrasound elastic image data generating unit 64, an MRI elastic image data generating unit 65, and a display image control unit 66.

The position calculator 61 calculates information (hereafter called "probe position information") about the position and inclination of the ultrasonic probe 2 in a three-dimensional space with the magnetic field generator 11 as an origin, based on the magnetic detection signal from the magnetic sensor 12. Further, the position calculator 61 calculates position information about echo data in the three-dimensional space, based on the probe position information.

The B-mode data and the physical quantity data are stored in the memory 62. The B-mode data and the physical quantity data are stored in the memory 62 as data set for every sound ray. The memory 62 includes a semiconductor memory such as a RAM (Random Access Memory), a ROM (Read Only Memory) or the like. Incidentally, the B-mode data and the physical quantity data may be stored even in the HDD 10.

Here, the echo signals (containing data generated based on echo signals) prior to being converted to B-mode image data and elastic image data to be described later will be assumed to be Raw Data. The B-mode data and physical quantity data stored in the memory 62 or the HDD 10 are raw data.

The echo signal subjected to the phasing-adding processing at the transmit-receive unit 3 may be stored in the HDD 10 as raw data.

MRI elastic image data generated at the MRI system 100 is stored in the memory 62 via the controller 9. The MRI elastic image data stored in the memory 62 is volume data and includes color information corresponding to the elasticity of the biological tissue. The MRI elastic image data stored in the memory 62 may contain information (nPa (where n: arbitrary numeric value, and Pa: pascal)) about the hardness H of the biological tissue calculated by the MRI system 100. The MRI elastic image data is one example illustrative of an embodiment of second elasticity display data. The MRI system 100 is one example illustrative of an embodiment of other medical image display apparatus. The information on the hardness H is one example illustrative of an embodiment of a second physical quantity.

Image data (MRI image data) of MRI images such as a T1 emphasized image, a T2 emphasized image, etc. generated by the MRI system 100 are also stored in the memory 62.

Incidentally, the MRI elastic image data and the MRI image data may be stored in the HDD 100.

The B-mode image data generating unit 63 scan-converts the B-mode data by a scan converter to generate B-mode image data having brightness information corresponding to the signal strength of each echo. The brightness information contained in the B-mode image data includes predetermined levels of gray (256 levels of gray).

Figure 4:
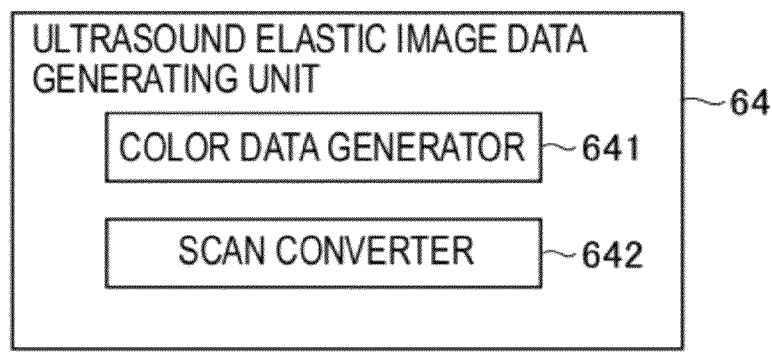
FIG. 4 is a block diagram illustrating a configuration of an elastic image data generating unit in the display controller shown in FIG. 3.

The ultrasound elastic image data generating unit 64 has a color data generator 641 and a scan converter 642 as shown in FIG. 4. The color data generator 641 generates color data CD based on the physical quantity data as will be described later. The color data CD has color information corresponding to the elasticity of the biological tissue. The color data is one example illustrative of an embodiment of first elasticity display data. The color data generator 64 is one example illustrative of an embodiment of a first elasticity display data generator. The color information is one example illustrative of an embodiment of display form information.

The scan converter 642 scan-converts the color data CD to generate ultrasound elastic image data.

The MRI elastic image data generating unit 65 generates MRI elastic image data including color information about an MRI elastic image displayed on the display unit 7, based on the information on the hardness H of the biological tissue calculated by the MRI system 100. The MRI elastic image data generated by the MRI elastic image data generating unit 65 has color information different from the MRI elastic image data generated by the MRI system 100 and stored in the memory 62. The details thereof will be described later. The MRI elastic image data is one example illustrative of an embodiment of second elasticity display data. The MRI elastic image data generating unit 65 is one example illustrative of an embodiment of a second elasticity display data generating unit.

Figure 5:
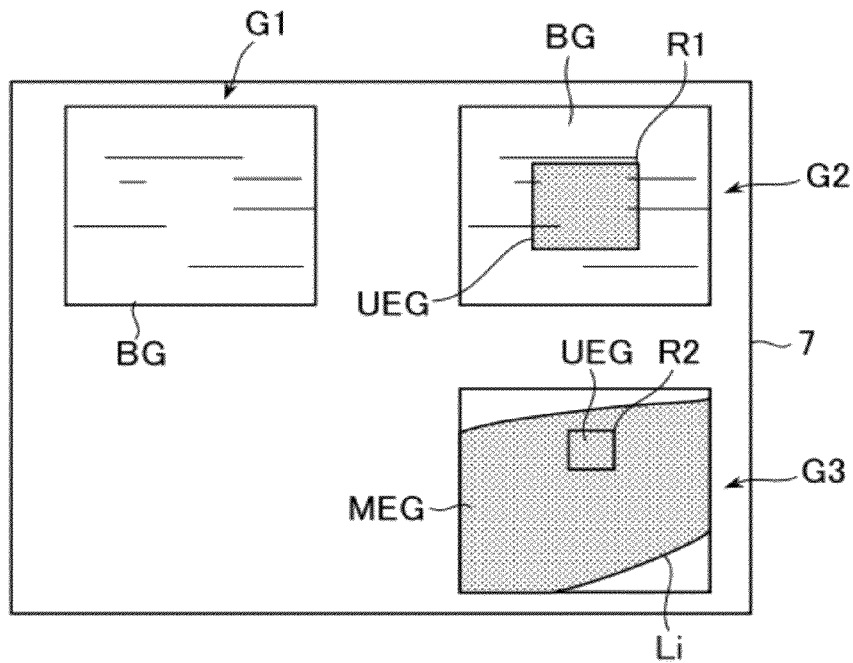
FIG. 5 is a diagram showing one example of a display unit on which medical images are displayed.

The display image control unit 66 allows the display unit 7 to display medical images G1, G2 and G3 as shown in FIG. 5, based on the B-mode image data, the ultrasound elastic image data and the MRI elastic image data generated by the MRI elastic image data generating unit 65 (display image control function). The medical image G1 includes a B-mode image BG, the medical image G2 includes a combined image of a B-mode image BG and an ultrasound elastic image UEG, and the medical image G3 includes a combined image of an MRI elastic image MEG and the ultrasound elastic image UEG. Incidentally, symbol Li in the medical image G3 indicates the liver. The medical image G3 is identical in cross-section to the medical images G1 and G2 in a biological tissue as will be described later, but the MRI elastic image MEG becomes an image wider in range than the ultrasound elastic image UEG and the B-mode image BG.

The ultrasound elastic image UEG and the MRI elastic image MEG are images each having a display form corresponding to the elasticity of the biological tissue. In the present example, they are images that include color corresponding to the elasticity of the biological tissue. The ultrasound elastic image UEG is one example illustrative of an embodiment of a first elastic image. The MRI elastic image MEG is one example illustrative of an embodiment of a second elastic image. Further, the display image control unit 66 is one example illustrative of an embodiment of a display image control unit, and the display image control function is one example illustrative of a display image control function.

The display image control unit 66 allows the display unit 7 to display, as the medical image G2, data combined and obtained by adding the B-mode image data and the ultrasound elastic image data together. In the medical image G2, the ultrasound elastic image UEG is disposed in such a manner that the B-mode image BG of the background is made transparent within a region of interest R1 set on the B-mode image BG. The region of interest R1 is one example illustrative of an embodiment of a display region for the first elastic image.

The display image control unit 66 causes the display unit 7 to display, as the medical image G3, an image obtained by superimposing the ultrasound elastic image UEG on a part of the MRI elastic image MEG. Here, "the superimposition" means that an image for the background is not displayed. The ultrasound elastic image UEG is displayed within its corresponding region of interest R2 set onto the MRI elastic image MEG.

Incidentally, the medical images G1 through G3 are images about the same section in the biological tissue, and the regions of interest ROI1 and R0I2 are set to the same position in the biological tissue.

Figure 7:
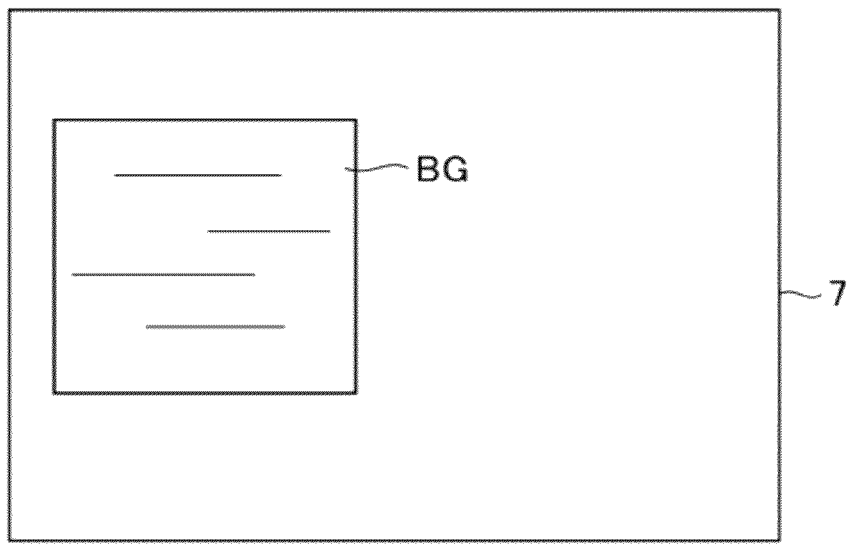
FIG. 7 is a diagram illustrating one example of the display unit on which a B-mode image is displayed.
Figure 8:
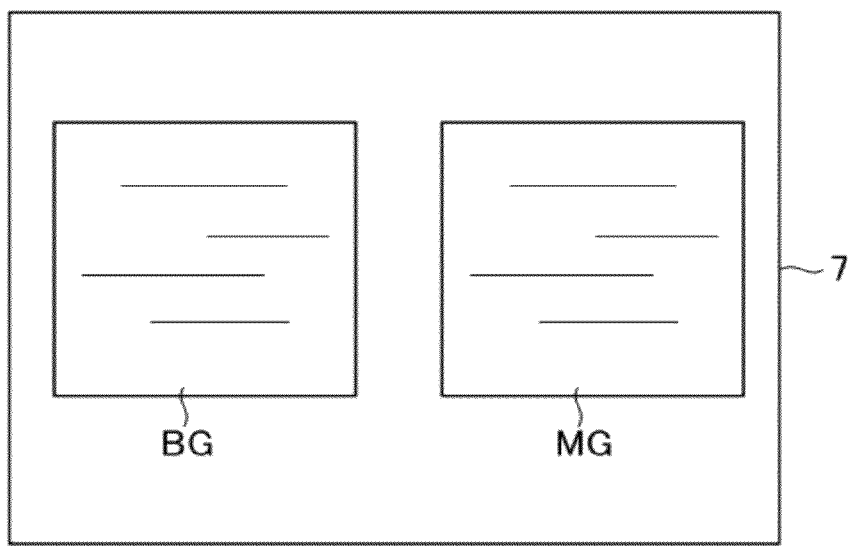
FIG. 8 is a diagram depicting one example of the display unit on which a B-mode image and an MRI image are displayed.

The display image control unit 66 may cause the display unit 7 to display only a B-mode image BG, based on the B-mode image data (refer to FIG. 7) or to display an MRI image MG, based on the MRI image data (refer to FIG. 8).

The display unit 7 includes an LCD (Liquid Crystal Display) or a CRT (Cathode Ray Tube) or the like. The operation unit 8 includes a keyboard and a pointing device (not shown) for causing an operator to input instructions and information. The operation unit 8 is one example illustrative of an embodiment of an input unit.

The controller 9 includes a CPU (Central Processing Unit). The controller 9 reads a control program stored in the HDD 10 and causes the control program to execute functions at the respective parts of the ultrasonic image display apparatus 1 starting with the physical quantity data generating function and the display image control function.

Figure 6:
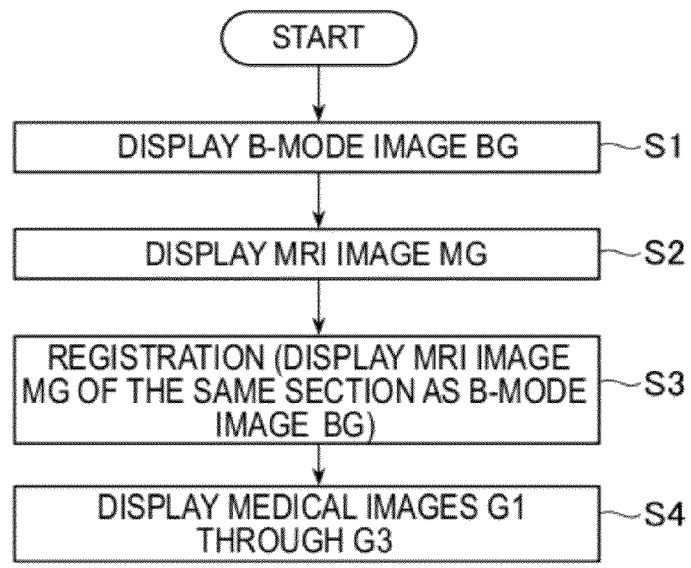
FIG. 6 is a flowchart showing the operation of the ultrasonic image display apparatus.

The operation of the ultrasonic image display apparatus 1 of the present embodiment at the time that the medical images G1 through G3 are displayed will now be explained based on the flowchart shown in FIG. 6. Upon displaying the medical images G1 through G3, processes of Steps S1 through S3 are performed to make registration between a coordinate system of an ultrasonic image (each of the B-mode image BG and the ultrasound elastic image UEG) and a coordinate system of each of the MRI elastic image MEG and the MRI image MG. Specifically, at Step S1, the ultrasonic probe 2 first transmits ultrasound to a biological tissue to receive each echo signal. Then, the display image control unit 66 causes the controller 7 to display a real-time B-mode image BG based on the echo signal as shown in FIG. 7.

Next, at Step S2, the display image control unit 66 allows the display unit 7 to display an MRI image MG based on the MRI image data stored in the HDD 10 or the memory 62 side by side with the B-mode image BG as shown in FIG. 8. The display image control unit 66 causes the display unit 7 to display an MRI image MG when there is an instruction input to the operation unit 8 by the operator.

Next, at Step S3, the coordinate system of the B-mode image BG and the coordinate system of the MRI image MG are brought into registration with each other. Specifically, the operator manipulates the operation unit 8 while comparing between the B-mode image BG and the MRI image MG displayed on the display unit 7 and allows the display unit 7 to display the corresponding MRI image MG having the same section as the real-time B-mode image BG. A decision as to whether they are identical in section to each other is made by allowing the operator to refer to a characteristic region, for example. Incidentally, assume now that the plane to be scanned by the ultrasonic probe 2 is parallel to a slice plane of the MRI image MG.

When the B-mode image BG and MRI image MG identical in section to each other are displayed, the operator designates an arbitrary point of the B-mode image BG on the display unit 7, using a track ball or the like of the operation unit 8. The operator designates a point to be considered to be the same position as the point designated at the B-mode image BG, even at the MRI image MG. Here, the MRI image data has position information. Thus, when the point considered to be identical in position between the B-mode image BG and the MRI image MG is designated as described above, the position of correspondence between the coordinate system of the B-mode image BG and the coordinate system of the MRI image MG is specified, so that a coordinate transformation between the coordinate system of the ultrasonic image and the coordinate system of each of the MRI image MG and the MRI elastic image MEG is enabled. After the completion of the above registration, the MRI image MG and the MRI elastic image MEG of the same section as the transmission/reception plane of the current ultrasound can be automatically displayed based on the position information calculated by the position calculator 61.

When the process of performing the registration at Steps S1 through S3 is terminated, the display image control unit 66 allows the display unit 7 to display the medical images G1 through G3 as shown in FIG. 5 at Step S4. At Step S4, the biological tissue is deformed by allowing the operator to repeat pressure and relaxation to the biological tissue through the ultrasonic probe 2 or allowing the ultrasonic probe 2 to apply acoustic radiation pressure. Then, the ultrasonic probe 2 performs the transmission/reception of ultrasound to and from the biological tissue in which this deformation is repeated. Then, the display image control unit 66 causes the display unit 7 to display the medical image G1 including the real-time B-mode image BG about the transmission/reception plane of the ultrasound by the ultrasonic probe 2 and to display the medical image G2 including the real-time B-mode image BG about the transmission/reception plane and the real-time ultrasound elastic image UEG about the transmission/reception plane. Further, the display image control unit 66 allows the display unit 7 to display the medical image G3 that includes the ultrasound elastic image UEG about the transmission/reception plane and the MRI elastic image MEG about the same section as the transmission/reception plane at the biological tissue.

The ultrasound elastic image UEG is displayed within the region of interest R1 set to the B-mode image BG and the region of interest R2 set to the MRI elastic image MEG. The regions of interest R1 and R2 are set so as to take the same position and range in the biological tissue. The regions of interest R1 and R2 are set by allowing the operator to manipulate the operation unit 8. More specifically, when either one of the regions of interest R1 and R2 is set, the other thereof is set to the same position at its set position and biological tissue. When the region of interest R1 is set at the B-mode image BG, for example, the region of interest R2 is set to the MRI elastic image MG so as to take the same position at the position to which the region of interest R1 is set and the biological tissue.

In the ultrasound elastic image UEG and the MRI elastic image MEG, portions thereof having the same elasticity at the biological tissue are represented in the same display form, i.e., the same color in the present embodiment.

Figure 9:
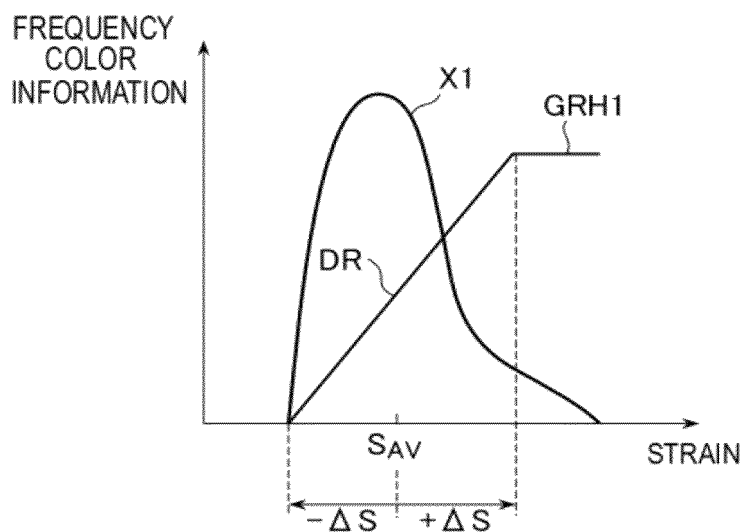
FIG. 9 is a diagram showing a distribution of strain in a region of interest which is target for the generation of an ultrasound elastic image, and a color information conversion graph.

Described in detail, the color data generator 641 converts strain's data configuring the physical quantity data into color information to generate color data. The color data generator 641 set, as shown in FIG. 9, a color information conversion graph GRH1 to which a predetermined number of color information corresponding to a strain S are assigned, to a distribution X1 of strain in the region of interest R1, and performs conversion to color information, based on the color information conversion graph GRH1.

Figure 10:
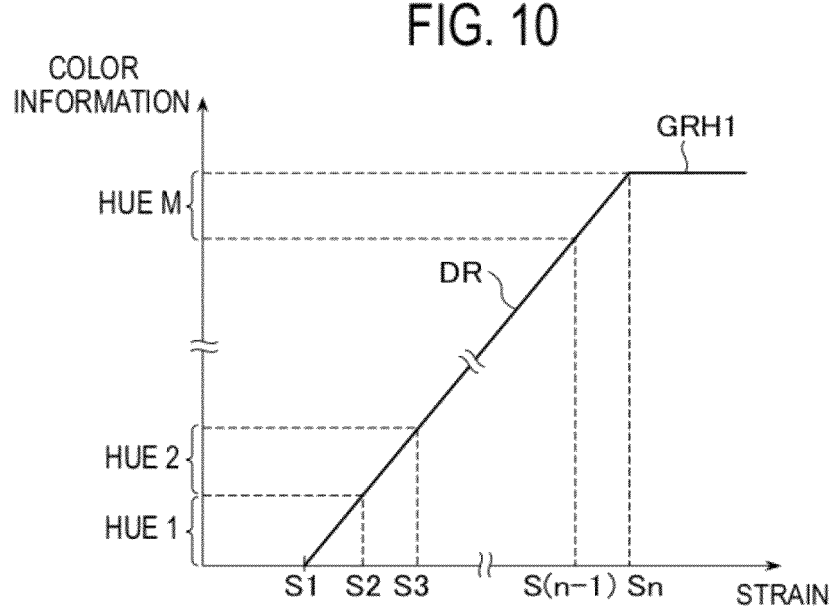
FIG. 10 is a diagram for describing the color information conversion graph shown in FIG. 9.

The color information conversion graph GRH1 will be explained. The color information conversion graph GRH1 is correlation information on the strain S and color. As shown in FIG. 10, the horizontal axis indicates the strain S, and the vertical axis indicates the color information. In the present embodiment, hue is used as the color information. The color information conversion graph GRH1 has M (M=256, for example) hue information of hues 1 through M. The color information conversion graph GRH1 is one example illustrative of an embodiment of first correlation information.

Here, assume that a portion having a gradient at the hue information conversion graph GRH1 is called "a dynamic range DR". In this dynamic range DR, the strain S is converted to hue information (hues 1 to M) different stepwise according to the value thereof. For example, the strain S is converted to the hue 1 when the strain S is greater than or equal to S1 and less than S2. When the strain S is greater than or equal to S2 and less than S3, the strain S is converted to the hue 2. When it is greater than or equal to S (n−1) and less than or equal to Sn, the strain S is converted to the hue M.

Incidentally, when a strain out of the dynamic range DR exists, this strain is converted to the same hue uniformly. In the present embodiment, a strain greater than the strain Sn corresponding to the horizontal portion in the hue information conversion graph GRH is converted to the hue M.

The dynamic range DR is set on the basis of the average value $S_{AV}$ of the strain S in the region of interest R1. Specifically, the color data generator 641 first calculates the average value $S_{AV}$ of the strain S in the region of interest R1. As shown in FIG. 9, the dynamic range DR is set to a strain range of $\pm\Delta S$ on the basis of the average value $S_{AV}$.

Based on the color information conversion graph GRH1 set in this manner, the color data generator 641 converts data about the strain S at the physical quantity data into hue information to generate color data. Then, the scan converter 642 scan-converts the color data to generate ultrasound elastic image data.

Figure 11:
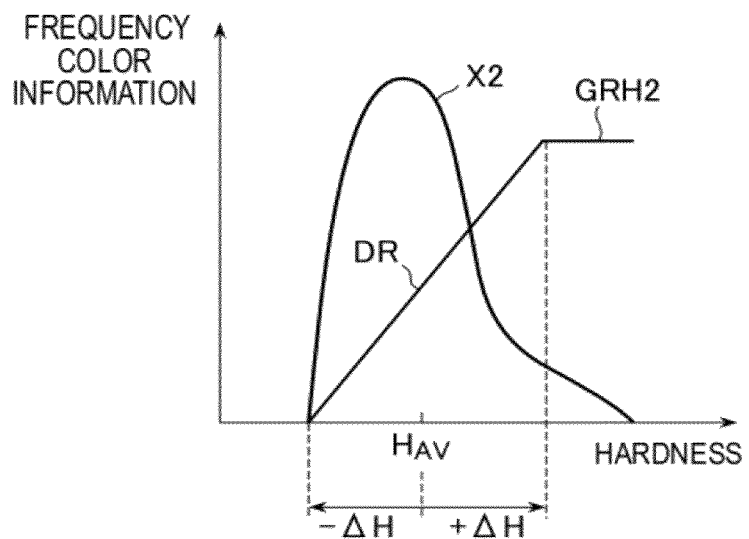
FIG. 11 is a diagram showing a distribution of hardness in a region of interest target for the generation of an MRI elastic image, and a color information conversion graph.

The MRI elastic image data generating unit 65 converts information about hardness H to color information to generate MRI elastic image data. The MRI elastic image data generating unit 65 sets, as shown in FIG. 11, a color information conversion graph GRH2 to which a predetermined number of color information corresponding to the hardness H are assigned, to a distribution X2 of hardness H in the region of interest R2, and performs conversion to color information, based on the color information conversion graph GRH2 to thereby generate MRI elastic image data. The color information conversion graph GRH2 is one example illustrative of an embodiment of second correlation information.

Figure 12:
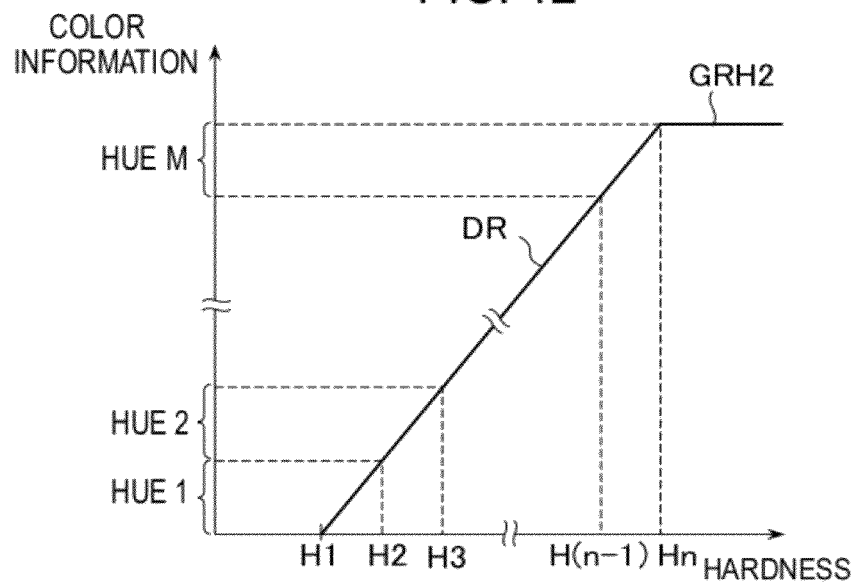
FIG. 12 is a diagram for describing the color information conversion graph shown in FIG. 11.

The color information conversion graph GRH2 is correlation information on the hardness H and color. As shown in FIG. 12, the horizontal axis indicates the hardness H, and the vertical axis indicates the color information. Even here, the color information is hue information. The color information conversion graph GRH2 has the same hue information (i.e., hues 1 through M) as the color information conversion graph GRH1.

In a dynamic range DR for the color information conversion graph GRH2, the color information is converted to the hue 1 when greater than or equal to H1 and less than H2. When the color information is greater than or equal to H2 and less than H3, it is converted to the hue 2. When the color information is greater than or equal to H (n−1) and less than Hn, it is converted to the hue M.

The dynamic range DR of the color information conversion graph GRH2 is set on the basis of the average value $H_{AV}$ of the hardness H in the region of interest R2. Specifically, the MRI elastic image data generating unit 65 first calculates the average value $H_{AV}$ of the hardness H in the region of interest R2. As shown in FIG. 11, the dynamic range DR is set to a hardness range of $\pm \Delta H$ on the basis of the average value $H_{AV}$.

Figure 13:
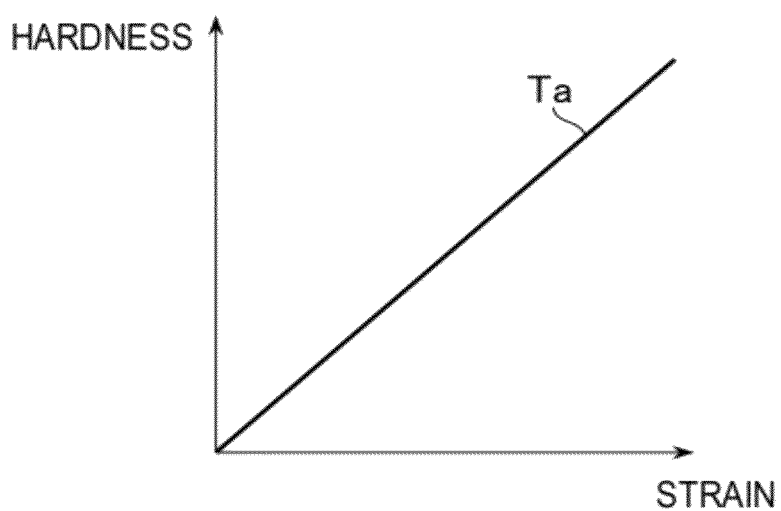
FIG. 13 is a diagram illustrating a table in which corresponding hardness and strain are defined.

Here, the ΔH indicative of the range of the hardness and the ΔS indicative of the range of the strain are respectively set to the ranges identical in terms of the elasticity of the biological tissue. As shown in FIG. 13, a table Ta in which the hardness H and strain S corresponding to each other are defined, is stored in the HDD 10 or the memory 62. This table Ta is correlation information in which the strain S and hardness H identical in terms of the elasticity of the biological tissue are defined. The table Ta is generated by measuring the strain S and hardness H using a phantom known in hardness in advance. The MRI elastic image data generating unit 65 determines the ΔH corresponding to the ΔS, based on the table Ta to set the dynamic range DR, thereby setting the color information conversion graph GRH2.

A range in which the hardness is greater than or equal to H1 and less than H2 is identical to a range in which the strain is greater than or equal to S1 and less than S2, in terms of the elasticity of the biological tissue. A range in which the hardness is greater than or equal to H2 and less than H3 is identical to a range in which the strain is greater than or equal to S2 and less than S3, in terms of the elasticity of the biological tissue. A range in which the hardness is greater than or equal to H (n−1) and not greater than Hn, is identical to a range in which the strain is greater than or equal to S (n−1) and not greater than Sn in terms of the elasticity of the biological tissue. Thus, at MRI elastic image data generated based on the color information conversion graph GRH2 and the ultrasound elastic image data, portions thereof identical to each other in the elasticity of the biological tissue have the same color information.

Incidentally, the setting of the dynamic range DR is not limited to the above. For example, the dynamic range DR may be set between the minimum and maximum values of the strain S in the region of interest R1 to generate the color information conversion graph GRH1, and the dynamic range DR may be set between the minimum and maximum values of the hardness H in the region of interest R2 to generate the color information conversion graph GRH2. Even where the color information conversion graphs GRH1 and GRH2 are generated in this way, the regions of interest R1 and R2 are the same portions in the biological tissue. For this reason, the portions having the same elasticity in the biological tissue become the same color information at the color data and MRI elastic image data generated based on the color information conversion graphs GRH1 and GRH2.

According to the ultrasonic image display apparatus 1 of the present embodiment described above, the portions having the same elasticity in the biological tissue are represented in the same color in terms of the ultrasound elastic image UEG and the MRI elastic image MEG. It is therefore possible to display an image useful for diagnosis.

Figure 14:
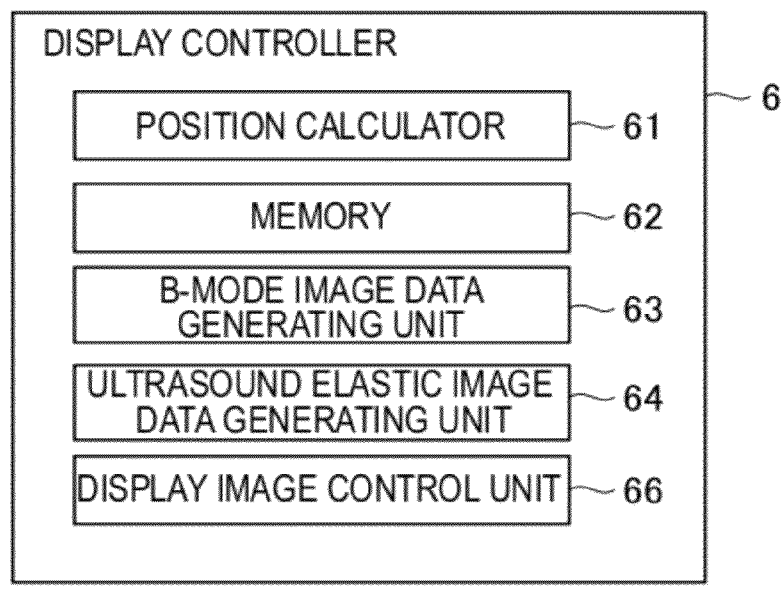
FIG. 14 is a block diagram showing a configuration of a display controller in a first modification of the embodiment.
Figure 15:
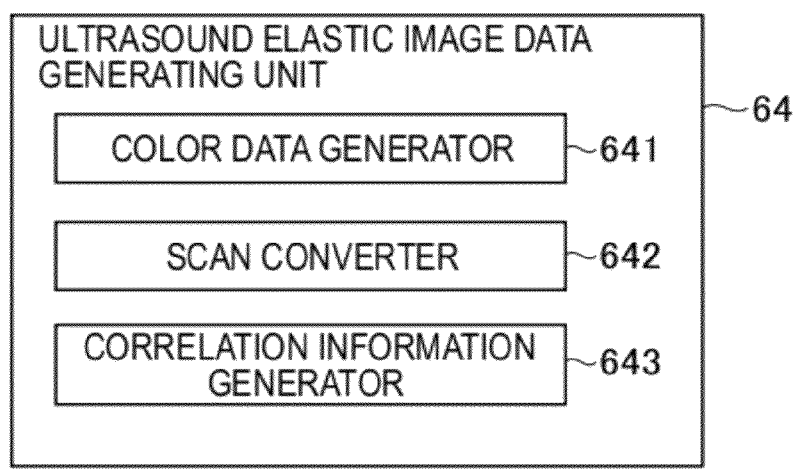
FIG. 15 is a block diagram illustrating a configuration of an ultrasound elastic image data generating unit in the first modification of the embodiment.

Modifications of the present embodiment will next be explained. A first modification will first be described. In the first modification, as shown in FIG. 14, the display controller 6 does not include the MRI elastic image data generating unit 65, but includes the position calculator 61, the memory 62, the B-mode image data generating unit 63, the ultrasound elastic image data generating unit 64, and the display image control unit 66. Further, as shown in FIG. 15, the ultrasound elastic image data generating unit 64 has a correlation information generator 643 in addition to the color data generator 641 and the scan converter 642.

Figure 16:
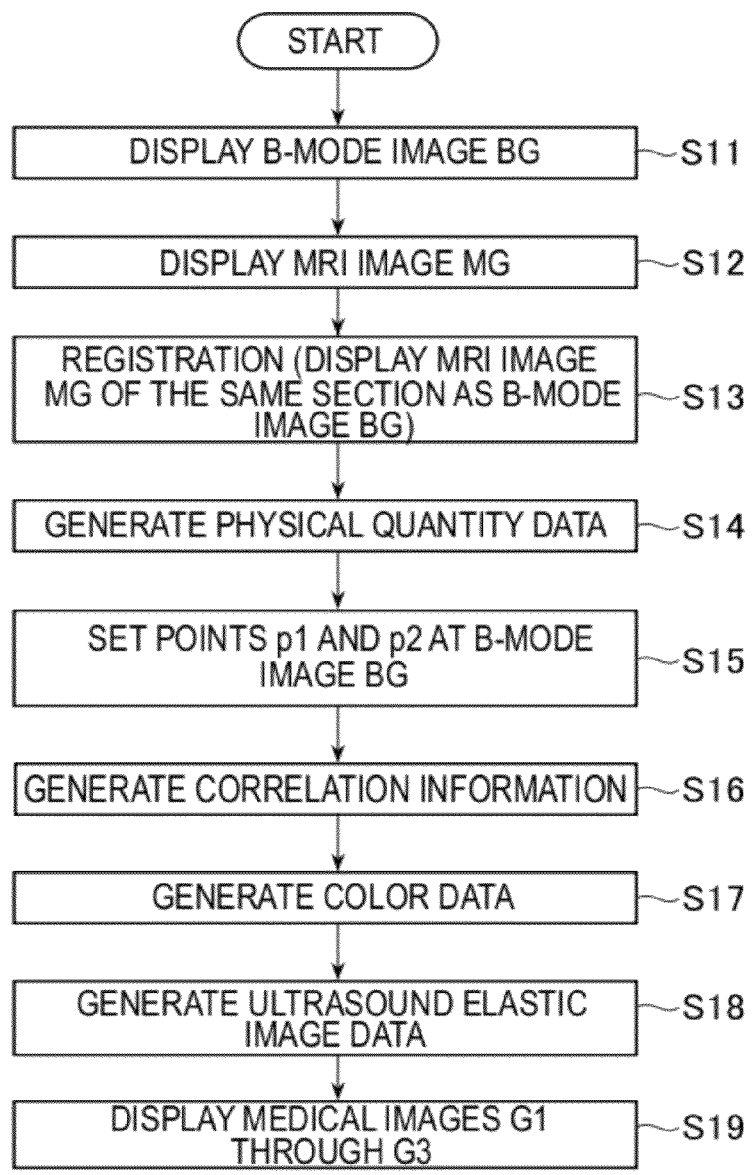
FIG. 16 is a flowchart showing the operation of an ultrasonic image display apparatus according to the first modification of the embodiment.

The operation of the present example will be explained based on the flowchart shown in FIG. 16. Steps S11 to S13 are identical to Steps S1 through S3 of FIG. 6 in processing, and their description will therefore be omitted. After the process of Step S13 is completed, the operator starts the transmission/reception of ultrasound by the ultrasonic probe 2 to and from the biological tissue whose deformation is repeated. Then, the physical quantity data generator 4 generates physical quantity data, based on the resulting echo signal.

Figure 17:
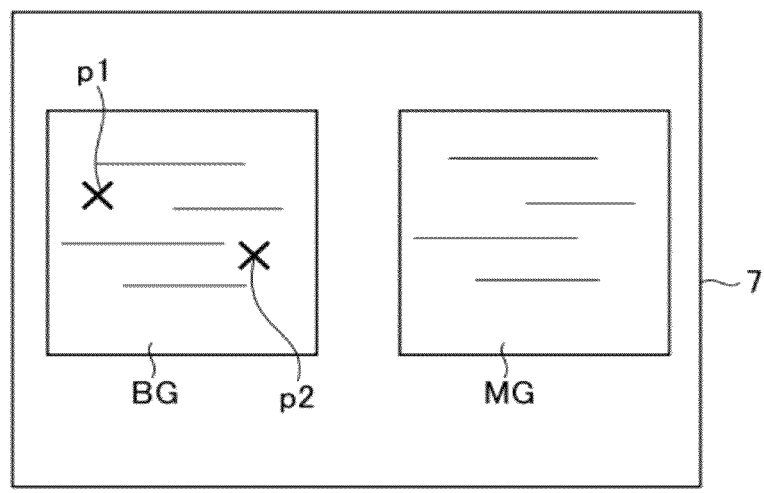
FIG. 17 is a diagram illustrating one example of the display unit on which arbitrary points are set to a B-mode image in the first modification of the embodiment.

Next, at Step S15, the operator manipulates the operation unit 8 to display a B-mode image BG having a desired section. Thereafter, the operator sets arbitrary points p1 and p2 at the B-mode image BG using a track ball or the like of the operation unit 8 as shown in FIG. 17. Incidentally, the points p1 and p2 may be set with respect to an image obtained by combining an ultrasound elastic image UEG based on ultrasound elastic image data generated based on the physical quantity data, and a B-mode image BG.

Next, at Step S16, correlation information indicative of a relationship of correspondence between the strain S and hardness H is generated. The correlation information is information in which the strain S and hardness H identical in the elasticity of the biological tissue are defined. Incidentally, in the present example, the correlation information on the strain S and hardness H is assumed to be unknown unlike the above.

Incidentally, the generation of the correlation information will be specifically explained. The correlation information generator 643 first specifies points p1' and p2' (not shown) corresponding to the point p1 and p2 at an MRI image MG. Each of the points corresponding to the points p1 and p2 means a point at the same position in the biological tissue.

Figure 18:
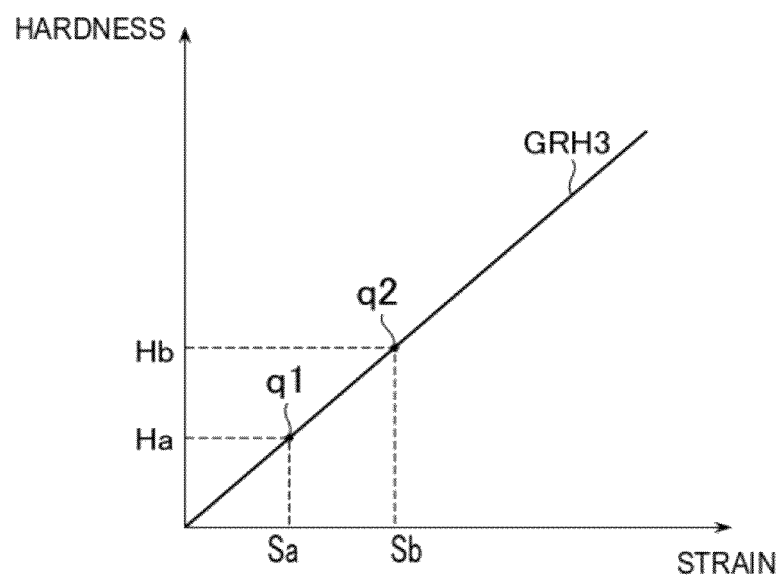
FIG. 18 is a diagram depicting a graph of correlation information of strain and hardness in the first modification.

A strain Sa at the point p1 and hardness Ha at the point p1' have the same elasticity. A strain Sb at the point p2 and hardness Hb at the point p2' have the same elasticity. Accordingly, the correlation information generator 643 plots a point q1 (Sa, Ha) and a point q2 (Sb, Hb) at a coordinate plane in which the horizontal axis indicates the strain S and the vertical axis indicates the hardness H, as shown in FIG. 18, and determines a graph GRH3 having a straight line that passes through these points q1 and q2, as correlation information. The correlation information that comprises the graph GRH3 is one example illustrative of an embodiment of physical quantity correlation information.

Next, at Step S17, the color data generator 641 converts the strain S of the physical quantity data to color information to generate color data. Specifically, the color data generator 641 first specifies the hardness H corresponding to the strain S of the physical quantity data, based on the graph GRH3 of the correlation information. Then, the color data generator 641 specifies color information corresponding to the specified hardness H, based on a color information conversion graph GRH4 (not shown) and converts the first physical quantity to the specified color information. The color data is one example illustrative of an embodiment of first elasticity display data. The color information conversion graph GRH4 is one example illustrative of an embodiment of correlation information.

The color information conversion graph GRH4 is used when the MRI system 100 converts the hardness H to color information to generate an MRI elastic image. Thus, at the color data generated by the color data generator 641 and the MRI elastic image data generated by the MRI system 100, the portions thereof having the same elasticity in the biological tissue are the same color information.

Incidentally, data about the color information conversion graph GRH4 are stored from the MRI system 100 to the HDD 10 or the memory 62.

Next, at Step S18, the scan converter 642 scan-converts the color data to generate ultrasound elastic image data. Then, at Step S19, the display image control unit 66 allows the display unit 7 to display the medical images G1 through G3 (refer to FIG. 5).

The ultrasound elastic image UEG in each of the medical images G2 and G3 is an image displayed based on the ultrasound elastic image data generated by the ultrasound elastic image data generating unit 64. The MRI elastic image MEG in the medical image G3 is an image displayed based on the MRI elastic image data generated at the MRI system 100 and stored in the memory 62 or the HDD 10. Thus, in the ultrasound elastic image UEG and the MRI elastic image MEG displayed on the display unit 7, the portions thereof having the same elasticity in the biological tissue are expressed in the same color information.

In the present example, the MRI elastic image data stored in the HDD 10 or the memory 62 and generated by the MRI system 100 is one example illustrative of an embodiment of second elasticity display data. The HDD 10 and the memory 62 are one example illustrative of an embodiment of a storage unit.

Incidentally, the B-mode image BG at each of the medical images G1 and G2, and the ultrasound elastic image UEG at the medical image G2 are real-time images. The B-mode image BG, the ultrasound elastic image UEG and the MRI elastic image MEG are images having the same section. Modifications to be described below are also similar.

Incidentally, the points p1 and p2 may be set at the MRI image MG. In this case, the points p1' and p2' are specified at the B-mode image BG.

There is no limitation to the case in which the points p1 and p2 are set and the correlation information included in the graph GRH3 is generated. The table Ta in which the corresponding hardness H and strain S are defined, may be used as the correlation information.

In the first modification, only the point p1 may be set at the B-mode image BG. In this case, the color data generator 641 specifies the point p1 and the point p1' corresponding to the MRI image MG, specifies color information corresponding to the hardness Ha adapted to the strain S at the point p1, based on the color information conversion graph GRH4, and converts data on the same strain S as the strain Sa at the point p1 in the physical quantity data to the specified color information. Thus, the portion having the same elasticity as that of the point p1 at the ultrasound elastic image UEG is represented in the same hue as that of the portion having the same elasticity as the point p1' at the MRI elastic image MEG. Accordingly, the case in which at the first and second images only some of the portions having the same elasticity in the biological tissue are represented in the same display form.

When only the point p1 is set, an ultrasound elastic image UEG of a portion harder in elasticity than the point p1 may be represented in the same hue as that of a portion harder than the point p1' at an MRI elastic image MEG.

A second modification of the present embodiment will next be explained. In the second modification, the display controller 6 has the configuration shown in FIG. 3, and the ultrasound elastic image data generating unit 64 has the configuration shown in the drawing.

Figure 19:
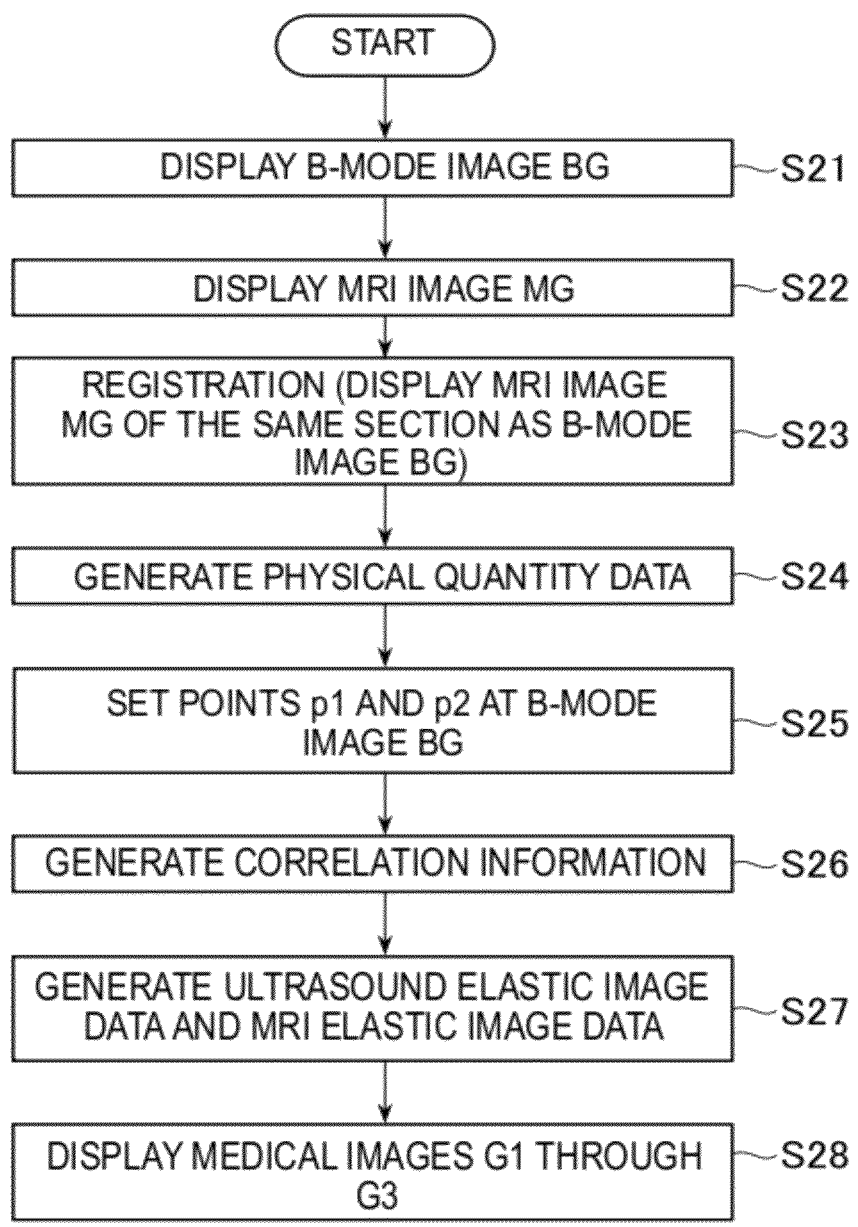
FIG. 19 is a flowchart showing the operation of an ultrasonic image display apparatus according to a second modification of the embodiment.

The operation of the present example will be explained based on the flowchart shown in FIG. 19. Steps S21 to S26 are identical to Steps S11 through S16 of FIG. 16 in processing, and their description will therefore be omitted. At Step S27, the ultrasound elastic image data generating unit 64 generates ultrasound elastic image data, based on the physical quantity data generated at Step S24, and the MRI elastic image data generating unit 65 converts information about the hardness H to color information to generate MRI elastic image data.

The generation of the ultrasound elastic image data will be explained. The color data generator 641 first generates color data, based on a color information conversion graph GRH5 (not shown and may be the same as the color information conversion graph GRH1) to which a predetermined number of color information each corresponding to a strain S are assigned, in a manner similar to Step S4 in the flowchart shown in FIG. 6. The color data is one example illustrative of an embodiment of first elasticity display data. The color data generator 641 is one example illustrative of an embodiment of a first elasticity display data generator. Then, the scan converter 642 scan-converts the color data to generate ultrasound elastic image data.

Next, the generation of the MRI elastic image data will be described. The MRI elastic image data generating unit 65 specifies a strain S corresponding to the hardness H calculated by the MRI system 100 and stored in the memory 62 or the HDD 10, based on the graph GRH3 (shown in FIG. 18) of the correlation information. Next, the MRI elastic image data generating unit 65 specifies color information corresponding to the specified strain S, based on the color information conversion graph GRH5 and converts the hardness H to the specified color information to generate MRI elastic image data. Accordingly, such portions as to have the same elasticity in the biological tissue are the same color information at the ultrasound elastic image data and the MRI elastic image data generated at Step S27.

Incidentally, the MRI elastic image data generated at Step S27 is one example illustrative of an embodiment of second elasticity display data. The MRI elastic image data generating unit 65 is one example illustrative of an embodiment of a second elasticity display data generating unit.

When the ultrasound elastic image data and the MRI elastic image data are generated at Step S27, the flowchart proceeds to a process of Step S28. At Step S28, the display image control unit 66 allows the display unit 7 to display the medical images G1 through G3.

The ultrasound elastic image UEG at each of the medical images G2 and G3 is an image displayed based on the ultrasound elastic image data generated at Step S27. The MRI elastic image MEG at the medical image G3 is an image displayed based on the MRI elastic image data generated at Step S27. Thus, at the ultrasound elastic image UEG and the MRI elastic image MEG displayed on the display unit 7, the portions thereof having the same elasticity in the biological tissue are expressed in the same color information.

Incidentally, even in the second modification, only the point p1 may be set at the B-mode image BG as with the first modification. In this case, the MRI elastic image data generating unit 65 specifies the point p1 and the point p1' corresponding to the MRI image MG, specifies color information corresponding to the strain Sa corresponding to the hardness Ha at the point p1', based on the color information conversion graph GRH5, and converts data on the same hardness H as the hardness Ha at the point p1' to the specified color information. Thus, at the MRI elastic image MEG, a portion thereof having the same elasticity as the point p1' is displayed in the same hue as the portion having the same elasticity as the point p1 at the ultrasound elastic image UEG.

When only the point p1 is set, an MRI elastic image MEG of a portion harder in elasticity than the point p1 may be represented in the same hue as that of a portion harder in elasticity than the point p1' at an ultrasound elastic image UEG.

Figure 20:
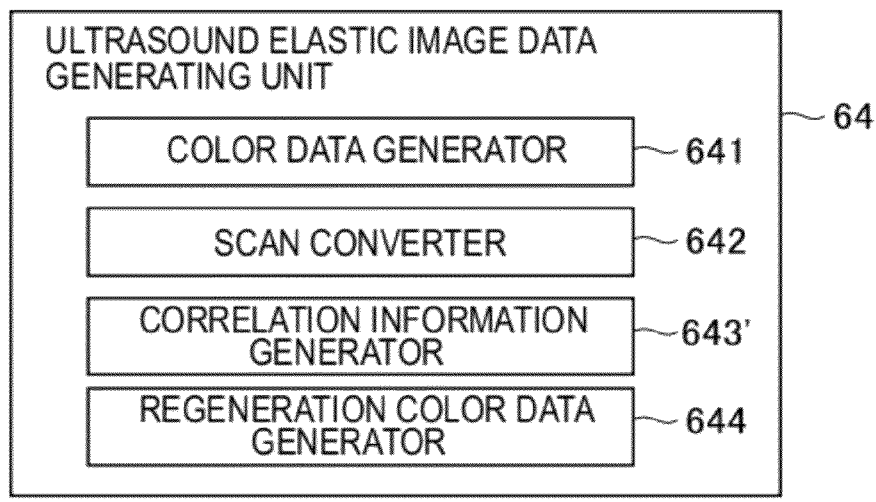
FIG. 20 is a block diagram illustrating a configuration of an ultrasound elastic image data generating unit of an ultrasonic image display apparatus according to a third modification of the embodiment.

A third modification will next be explained. In the third modification, the display controller 6 is the same configuration as FIG. 1. The ultrasound elastic image data generating unit 64 has, as shown in FIG. 20, a correlation information generator 643' and a regeneration color data generator 644 in addition to the color data generator 641 and the scan converter 642. The regeneration color data generator 644 is one example illustrative of an embodiment of a third elasticity display data generator.

Figure 21:
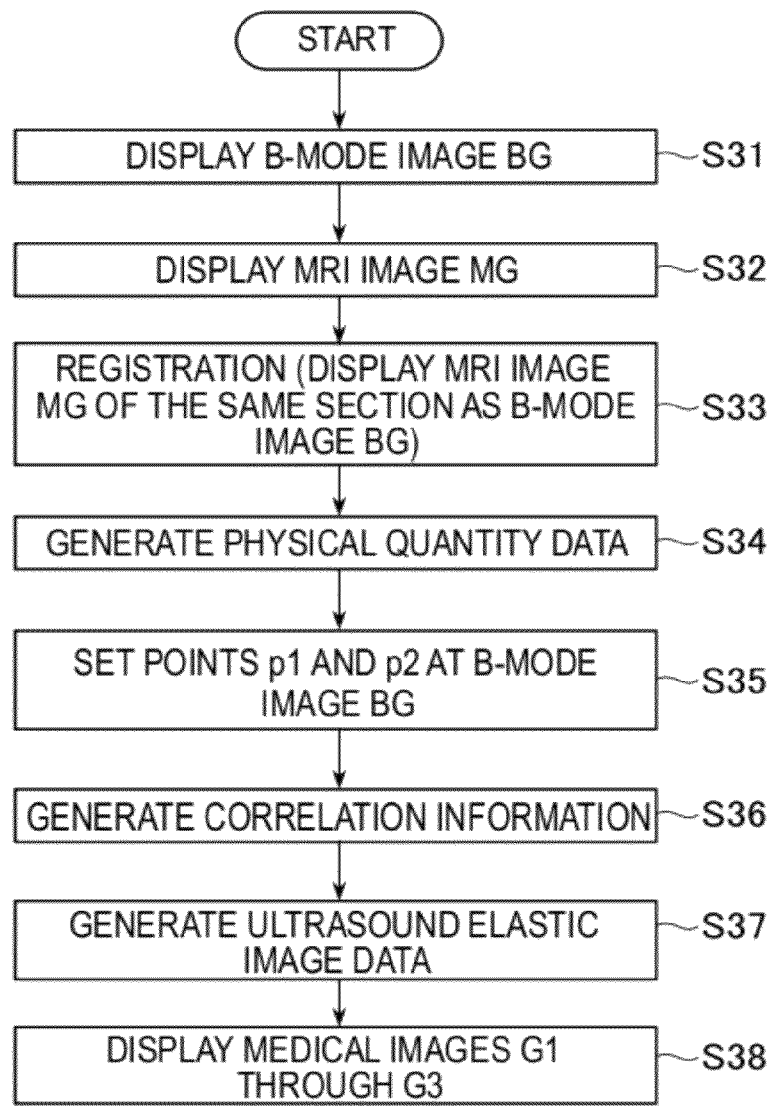
FIG. 21 is a flowchart showing the operation of the ultrasonic image display apparatus according to the third modification.

The operation of the present example will be explained based on the flowchart shown in FIG. 21. Steps S31 to S35 are identical to Step S11 through S15 of FIG. 16 and Steps S21 through S25 of FIG. 19 in processing, and their description will therefore be omitted. When points p1 and p2 are set at Step S35, the correlation information generator 643' generates correlation information indicative of a relationship of correspondence between color information of color data and color information of MRI elastic image data at Step S36. The correlation information is one example illustrative of an embodiment of display form correlation information.

The color data generator 641 generates the color data, based on the physical quantity data generated at Step S34. The color data generator 641 generates color data based on the color information conversion graph GRH5. The color data is one example illustrative of an embodiment of first elasticity display data. The color data generator 641 is one example illustrative of an embodiment of a first elasticity display data generator.

The MRI elastic image data is of the data generated by the MRI system 100 and stored in the memory 62 or the HDD 10.

Incidentally, the scan converter 642 may scan-convert the color data generated by the color data generator 641 to generate ultrasound elastic image data. At Step S35, the points p1 and p2 may be set at an image obtained by combining an ultrasound elastic image UEG based on the ultrasound elastic image data and a B-mode image BG. The ultrasound elastic image UEG in this case is one example illustrative of an embodiment of an elastic image of a biological tissue based on the first elasticity display data.

The correlation information in the present example is information in which color information identical in the elasticity of the biological tissue are defined based on the color data and the MRI elastic image data. Specifically, the correlation information generator 643' first specifies points p1' and p2' corresponding to the points p1 and p2 at the MRI image MG in a manner similar to Step S16 (refer to FIG. 16) and Step S26 referred to above.

Incidentally, the display unit 7 is caused to display an ultrasound elastic image UEG and an MRI elastic image MEG. Then, the points p1 and p2 may be set to the ultrasound elastic image UEG, and the points p1' and p2' corresponding to the points p1 and p2 may be specified at the MRI elastic image MEG. In this case, the ultrasound elastic image UEG displayed here is an image based on the color data generated by the color data generator 641. Further, the MRI elastic image MEG displayed here is an image based on the MRI elastic image data generated by the MRI system 100.

The points p1 and p1' have the same elasticity because they are at the same position in the biological tissue. Accordingly, color information C1 at the point p1 and color information C1' at the point p1' have the same elasticity. Further, since the points p2 and p2' are placed in the same position in the biological tissue, they have the same elasticity. Accordingly, color information C2 at the point p2 and color information C2' at the point p2' have the same elasticity. The correlation information generator 643' plots a point q3 (C1, C1') and a point q4 (C2, C2') at a coordinate plane in which the horizontal axis indicates the color information of the color data and the vertical axis indicates the color information of the MRI elastic image data, and determines a graph GRH6 having a straight line that passes through these points q3 and q4, as correlation information.

Next, at Step S37, the ultrasound elastic image data generating unit 64 generates ultrasound elastic image data. This will be explained in detail. The regeneration color data generator 644 first generates regeneration color data based on the color data generated by the color data generator 641. Specifically, the regeneration color data generator 644 first specifies color information on the MRI elastic image data corresponding to color information on the color data based on the graph GRH6 of the correlation information. Then, the regeneration color data generator 644 converts the color information of the color data to the corresponding color information on the MRI elastic image data specified based on the graph GRH6 to generate regeneration color data. The regeneration color data is one example of an embodiment of third elasticity display data.

A portion having the same elasticity in the biological tissue is of the same color information at each of the regeneration color data and the MRI elastic image data.

Next, the scan converter 642 scan-converts the regeneration color data to generate the ultrasound elastic image data.

When the ultrasound elastic image data is generated at Step S37, the display image control unit 66 allows the display unit 7 to display the medical images G1 through G3 at Step S38 (refer to FIG. 5).

The ultrasound elastic image UEG at each of the medical images G2 and G3 is an image displayed based on the ultrasound elastic image data generated at Step S37. The MRI elastic image MEG at the medical image G3 is an image displayed based on the MRI elastic image data generated by the MRI system 100 and stored in the memory 62 or the HDD 10. Thus, at each of the ultrasound elastic image UEG and the MRI elastic image MEG both displayed on the display unit 7, a portion having the same elasticity in the biological tissue is expressed in the same color information.

Incidentally, only the point p1 may be set even in the third modification. In this case, the regeneration color data generator 644 specifies a point p1' corresponding to the point p1 at the MRI image MG, and converts the same color information as that of the point p1 to color information of the MRI elastic image data at the point p1' at the color data. Thus, at the ultrasound elastic image UEG, a portion having the same elasticity as that of the point p1 is displayed in the same hue as that of a portion having the same elasticity as the point p1' at the MRI elastic image MEG.

When only the point p1 is set, an ultrasound elastic image UEG of a portion harder in elasticity than the point p1 may be displayed in the same hue as that of a portion harder than the point p1' at an MRI elastic image MEG.

Figure 23:
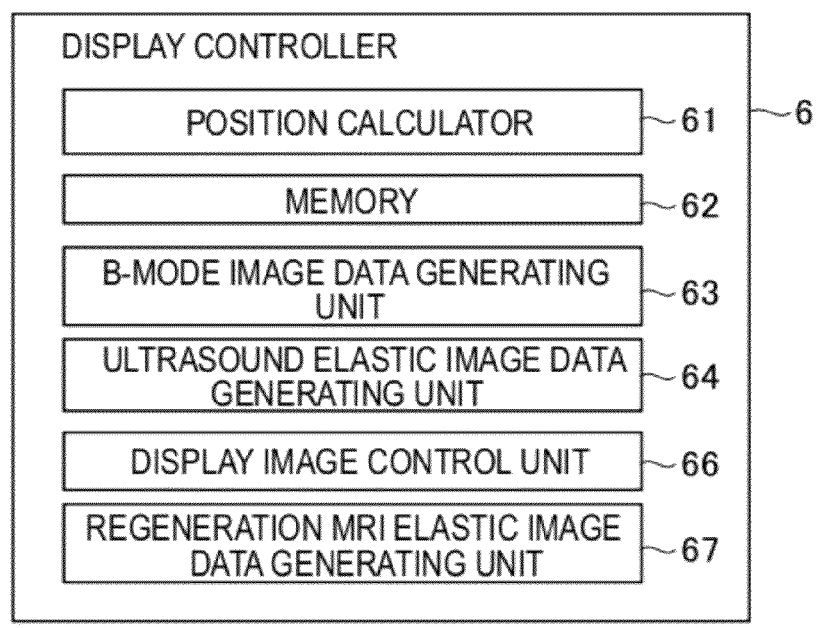
FIG. 23 is a block diagram showing a configuration of a display controller of an ultrasonic image display apparatus according to a fourth modification of the embodiment.
Figure 24:
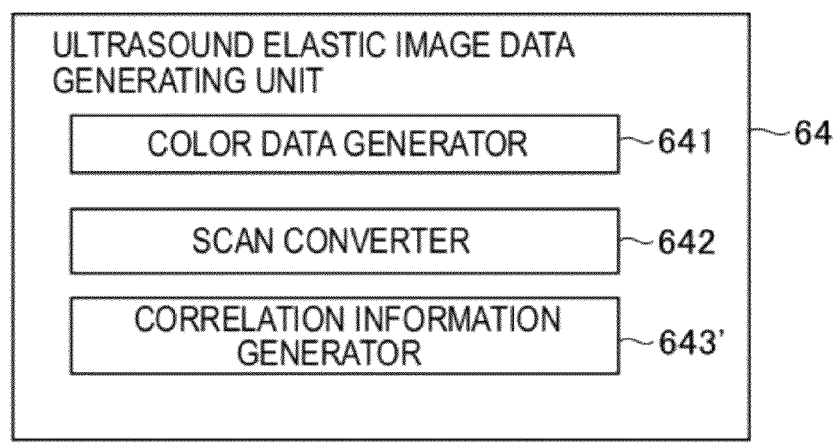
FIG. 24 is a block diagram illustrating a configuration of an ultrasound elastic image data generating unit of the ultrasonic image display apparatus according to the fourth modification.

A fourth modification will next be explained. In the fourth modification, the display controller 6 has, as shown in FIG. 23, a regeneration MRI elastic image data generating unit 67 in addition to the position calculator 61, the memory 62, the B-mode image data generating unit 63, the ultrasound elastic image data generating unit 64, and the display image control unit 66. The regeneration MRI elastic image data generating unit 67 is one example illustrative of an embodiment of a fourth elasticity display data generating unit. The ultrasound elastic image data generating unit 64 has the color data generator 641, the scan converter 642 and the correlation information generator 643' as shown in FIG. 24.

Figure 25:
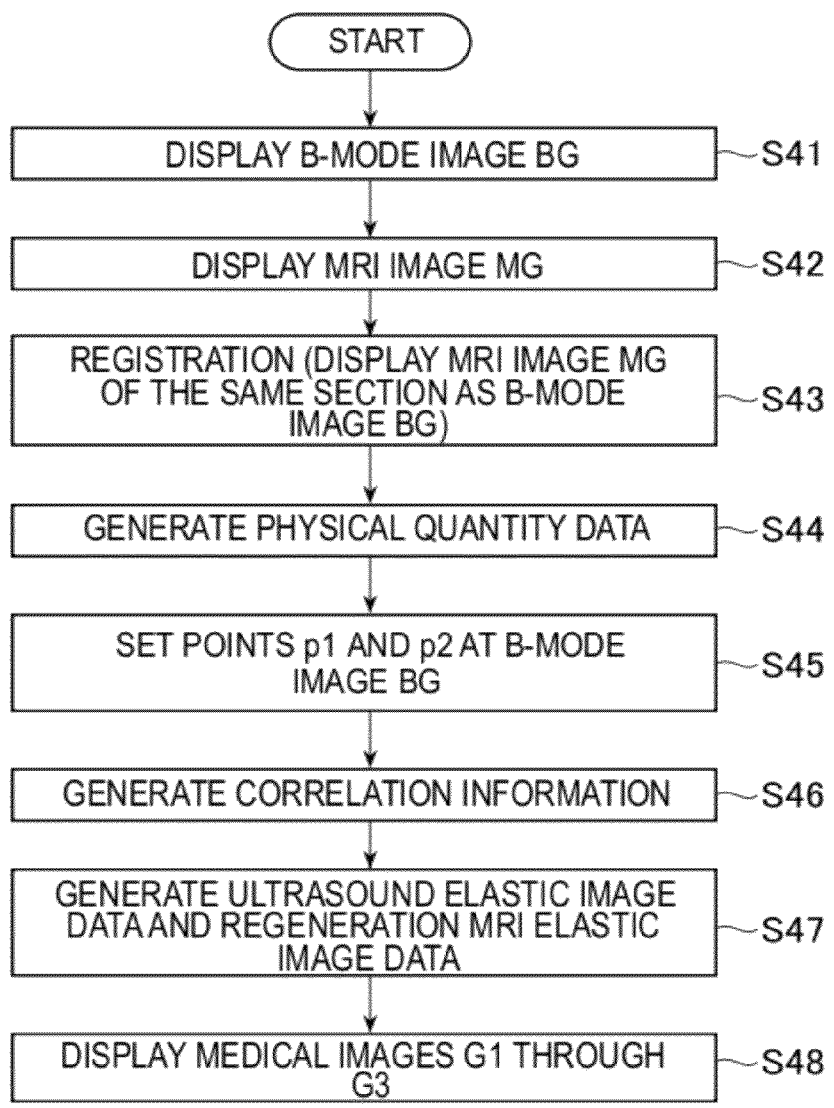
FIG. 25 is a flowchart showing the operation of the ultrasonic image display apparatus according to the fourth modification.

The operation of the present example will be explained based on the flowchart shown in FIG. 25. Steps S41 to S46 are identical to Step S31 through S36 of FIG. 21 in processing, and their description will therefore be omitted. At Step S47, the ultrasound elastic image data generating unit 64 generates ultrasound elastic image data. The regeneration MRI elastic image data generating unit 67 generates regeneration MRI elastic image data, based on the MRI elastic image data generated at the MRI system 100 and stored in the memory 62 or the HDD 10.

Figure 22:
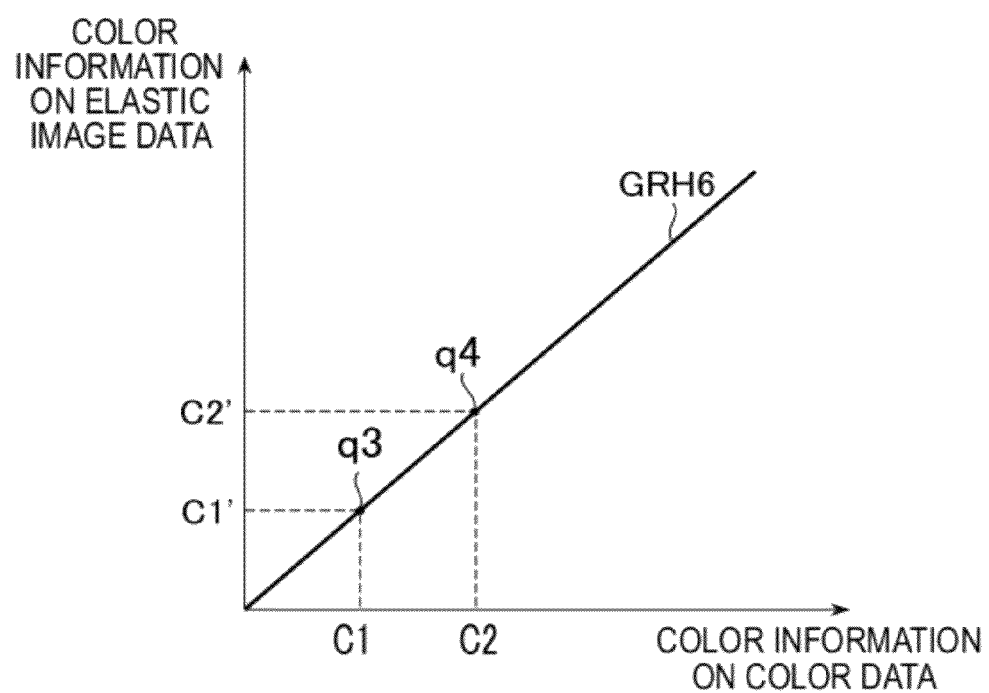
FIG. 22 is a diagram illustrating a graph of correlation information of strain and hardness in the third modification.

In the ultrasound elastic image data generating unit 64, the scan converter 642 scan-converts the color data generated by the color data generator 641 to generate the ultrasonic elastic image data. The regeneration MRI elastic image data generating unit 67 specifies color information of the color data corresponding to color information of the MRI elastic image data, based on the graph GRH6 (refer to FIG. 22) of the correlation information. Then, the regeneration MRI elastic image data generating unit 67 converts the color information of the MRI elastic image data to the color information of the color data specified based on the graph GRH6 to generate regeneration MRI elastic image data. The regeneration MRI elastic image data is one example illustrative of an embodiment of fourth elasticity display data.

A portion having the same elasticity in a biological tissue is the same color information at each of the regeneration MRI elastic image data and the color data.

Next, at Step S48, the display image control unit 66 causes the display unit 7 to display the medical images G1 through G3 (refer to FIG. 5).

The ultrasound elastic image UEG at each of the medical images G2 and G3 is an image displayed based on the ultrasound elastic image data generated at Step S47. The MRI elastic image MEG at the medical image G3 is an image displayed based on the regeneration MRI elastic image data generated at Step S47. Thus, at each of the ultrasound elastic image UEG and the MRI elastic image MEG both displayed on the display unit 7, a portion having the same elasticity in the biological tissue is expressed in the same color information.

Incidentally, even in the present example, an MRI elastic image data MEG based on the MRI elastic image data generated by the MRI system 100 may be displayed as with the third modification. The MRI elastic image MEG in this case is one example illustrative of an embodiment of an elastic image of a biological tissue based on second elasticity display data.

Incidentally, only the point p1 may be set even in the fourth modification. In this case, the regeneration MRI elastic image data generating unit 67 specifies a point p1' corresponding to the point p1 at the MRI image MG, and converts the same color information as that of the point p1' to color information of the color data at the point p1 at the MRI elastic image data. Thus, at the MRI elastic image MEG, a portion having the same elasticity as that of the point p1' is displayed in the same hue as that of a portion having the same elasticity as the point p1 at the ultrasound elastic image UEG.

Although the invention has been described by the respective embodiments as described above, it is needless to say that the invention may be modified and implemented in various ways within the scope not departing from the gist thereof. For example, the physical quantity data generator 5 may calculate a displacement due to the deformation of a biological tissue, elastic modulus or the like instead of the strain as a physical quantity related to the elasticity of the biological tissue. Further, acoustic radiation pressure is applied to the biological tissue to generate a shear wave in the biological tissue. The hardness (Pa: Pascal) of the biological tissue may be calculated as a physical quantity related to the elasticity of the biological tissue, based on the velocity of the shear wave. Incidentally, the velocity of the shear wave can be calculated based on an echo signal of ultrasound. Further, the physical quantity related to the elasticity of the biological tissue may be calculated by another known method.

Figure 26:
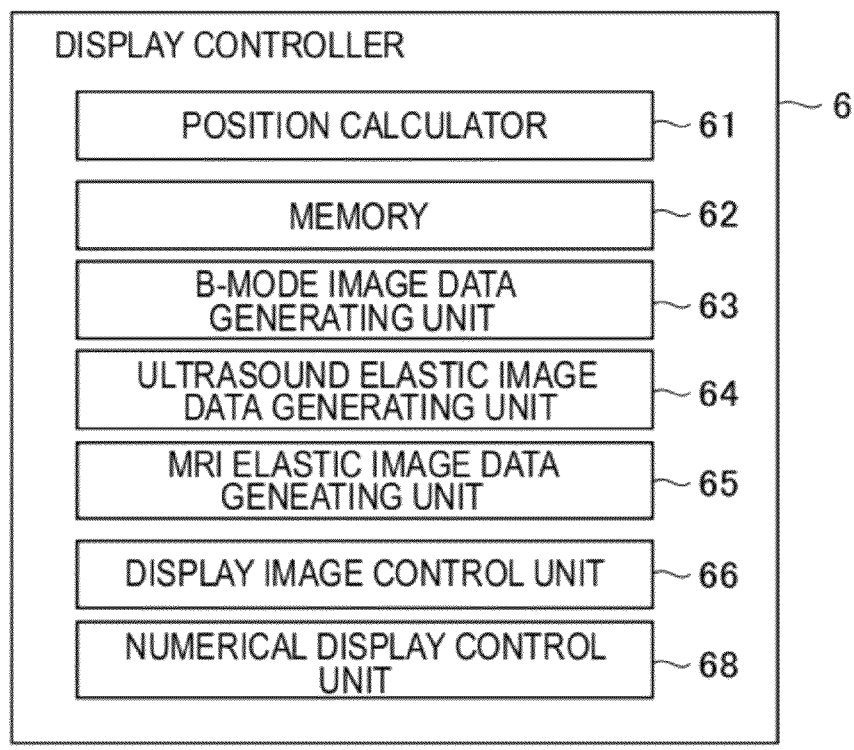
FIG. 26 is a block diagram depicting another example of the configuration of the display controller of the ultrasonic image display apparatus according to the embodiment.
Figure 27:
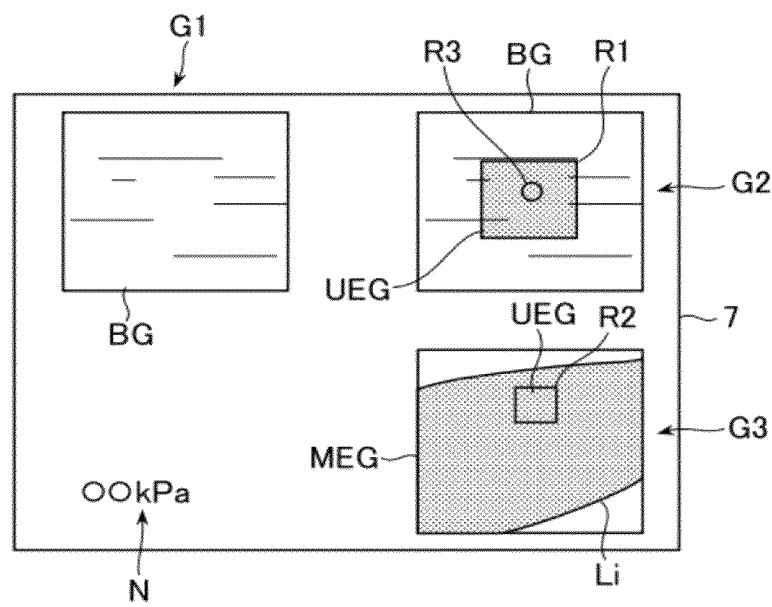
FIG. 27 is a diagram showing one example of the display unit on which a measuring region is set.

As shown in FIG. 26, the display controller 6 may have a numerical display control unit 68 which allows the display unit 7 to display the value N of the hardness H calculated by the MRI system 100. In this case, when the operator sets a measurement region R3 using the track ball or the like of the operation unit 8 at the ultrasound elastic image UEG at the medical image G2 as shown in FIG. 27, the numerical display control unit 68 specifies the same position as the measurement region R3 in the biological tissue at an MRI elastic image MEG, and allows the display unit 7 to display the value N of hardness H at its position. The numerical display control unit 68 is one example illustrative of an embodiment of a numerical display control unit.

Incidentally, the display controller 6 shown in FIG. 26 has a configuration in which the numerical display control unit 68 is added to the configuration of the display controller 6 shown in FIG. 3, but may have a configuration in which the numerical display control unit 68 is added to the configuration of the display controller 6 shown in each of FIGS. 14 and 23 (not shown).

Figure 28:
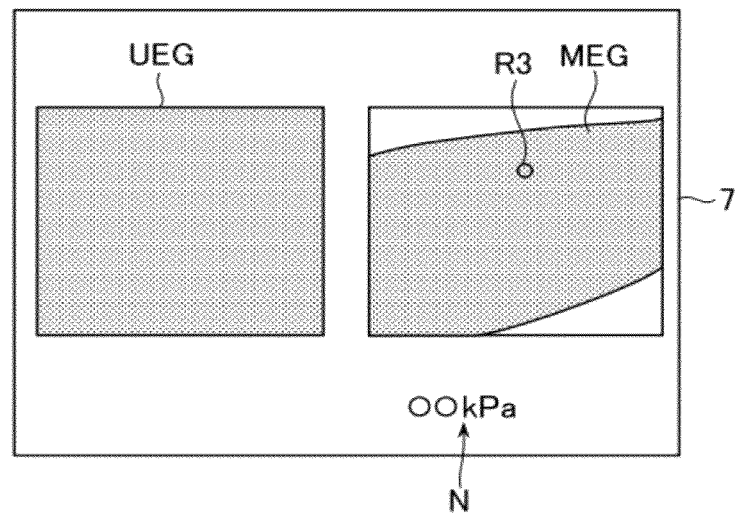
FIG. 28 is a diagram showing another example of the display unit on which a measuring region is set.

As shown in FIG. 28, the display image control unit 66 may cause the display unit to display an ultrasound elastic image UEG and an MRI elastic image MEG side by side with each other. The operator may set the measurement region R3 to the MRI elastic image MEG using the operation unit 8, and the numerical display control unit 68 may cause the display unit to display the value N of hardness H of the measurement region R3.

The display image control unit 66 may place a medical image G1 including the B-mode image BG, a medical image G2 including a combined image of the B-mode image BG and the ultrasound elastic image UEG, and a medical image G3 including a combined image of the MRI elastic image MEG and the ultrasound elastic image UEG side by side and cause the display unit 7 to display an MRI image although not illustrated in particular.

Many widely different embodiments of the invention may be configured without departing from the spirit and the scope of the present invention. It should be understood that the present invention is not limited to the specific embodiments described in the specification, except as defined in the appended claims.

The invention claimed is:

1. A medical image display apparatus for displaying medical images of a biological tissue, said display apparatus comprising:
- a physical quantity calculator configured to calculate a first physical quantity related to elasticity of the biological tissue;
- a display image control unit configured to display a first elastic image having a display form corresponding to the first physical quantity calculated by the physical quantity calculator and a second elastic image having a display form corresponding to a second physical quantity related to elasticity of the biological tissue calculated by another medical image display apparatus as the medical images, wherein the first physical quantity is different than the second physical quantity,
- wherein the display image control unit is further configured to display, as the first and second elastic images, images in which portions having a same elasticity in the biological tissue are displayed in a same display form, the images based on physical quantity correspondence information in which the first physical quantity and the second physical quantity are identical to each other relative to the elasticity of the biological tissue,
- a first elasticity display data generator configured to convert the first physical quantity to display form information on the first elastic image and to generate first elasticity display data including the display form information; and
- a second elasticity display data generator configured to convert the second physical quantity to display form information on the second elastic image and to generate second elasticity display data including the display form information,
- wherein the first elasticity display data generator and the second elasticity display data generator respectively are configured to generate the first elasticity display data and the second elasticity display data such that portions having the same elasticity in the biological tissue have the same display form information at the first elasticity display data and the second elasticity display data,
- wherein the display image control unit is configured to display the first elastic image based on the first elasticity display data and the second elastic image based on the second elasticity display data,
- wherein the first elasticity display data generator is configured to set first corresponding information of the first physical quantity and the display form information on the first elastic image based on a distribution of the first physical quantity calculated by the physical quantity calculator, and to convert from the first physical quantity to the display form information based on the first corresponding information,
- wherein the second elasticity display data generator is configured to set second corresponding information of the second physical quantity and the display form information on the second elastic image based on a distribution of the second physical quantity calculated by the other medical image display apparatus, and to convert from the second physical quantity to the display form information based on the second corresponding information, and
- wherein the first elasticity display data generator and the second elasticity display data generator respectively are configured to set the first corresponding information and the second corresponding information based on the physical quantity correspondence information such that the first physical quantity and the second physical quantity having the same elasticity in the biological tissue are converted to the same display form information.

2. The medical image display apparatus according to claim 1, further comprising:
- a storage unit configured to store second elasticity display data including display form information corresponding to the second physical quantity and generated by the other medical image display apparatus, and
- a first elasticity display data generator configured to specify the second physical quantity corresponding to the first physical quantity based on physical quantity correspondence information, to convert the first physical quantity to the display form information corresponding to the second physical quantity, and to generate the first elasticity display data including display form information corresponding to the first physical quantity,
- wherein the display image control unit is configured to display the first elastic image based on the first elasticity display data and the second elastic image based on the second elasticity display data.

3. The medical image display apparatus according to claim 2, wherein the first elasticity display data generator is configured to covert from the first physical quantity corresponding to the second physical quantity to the display form information based on corresponding information of the second physical quantity and to display form information on the second elastic image.

4. The medical image display apparatus according to claim 3, wherein the corresponding information is acquired from the other medical image display apparatus and stored in the storage unit.

5. The medical image display apparatus according to claim 1,
- wherein the first elasticity display data generator is further configured to convert the first physical quantity to display form information on the first elastic image and to generate first elasticity display data including the display form information; and
- wherein the second elasticity display data generator is further configured to specify the first physical quantity corresponding to the second physical quantity based on physical quantity correspondence information, to convert the second physical quantity to the display form information corresponding to the first physical quantity, and to generate the second elasticity display data including display form information corresponding to the second physical quantity,
- wherein the display image control unit is configured to display the first elastic image based on the first elasticity display data and the second elastic image based on the second elasticity display data.

6. The medical image display apparatus according to claim 5, wherein the second elasticity display data generator is configured to convert from the second physical quantity corresponding to the first physical quantity to the display form information based on corresponding information of the first physical quantity and to display form information on the first elastic image.

7. The medical image display apparatus according to claim 1, wherein the display image control unit is configured to display a combined image of the first elastic image and the second elastic image.

8. The medical image display apparatus according to claim 1, further comprising:

an input unit configured to input a setting a measurement region at the first elastic image or the second elastic image; and a numerical display control unit configured to display a numeric value of the second physical quantity at the measurement region set at the input unit.

9. A method for displaying medical images of a biological tissue, said method comprising:

calculating a first physical quantity related to elasticity of the biological tissue;

calculating a first elastic image having a display form corresponding to the first physical quantity by a medical image display apparatus;

calculating a second elastic image having a display form corresponding to a second physical quantity related to elasticity of the biological tissue by another medical image display apparatus to be displayed as the medical images, wherein the first physical quantity is different than the second physical quantity;

displaying, as the first and second elastic images, images in which portions having a same elasticity in the biological tissue are displayed in a same display form, the images based on physical quantity correspondence information in which the first physical quantity and the second physical quantity are identical to each other relative to the elasticity of the biological tissue;

converting the first physical quantity to display form information on the first elastic image and generating first elasticity display data including the display form information;

converting the second physical quantity to display form information on the second elastic image and generating second elasticity display data including the display form information, wherein the first elasticity display data and the second elasticity display data are generated such that portions having the same elasticity in the biological tissue have the same display form information as the first elasticity display data and the second elasticity display data;

displaying the first elastic image based on the first elasticity display data and the second elastic image based on the second elasticity display data;

setting first corresponding information of the first physical quantity and the display form information on the first elastic image based on a distribution of the first physical quantity, and converting from the first physical quantity to the display form information based on the first corresponding information;

setting second corresponding information of the second physical quantity and the display form information on the second elastic image based on a distribution of the second physical Quantity calculated by the other medical image display apparatus, and coverting from the second physical quantity to the display form information based on the second corresponding information, and setting the first corresponding information and the second corresponding information based on the physical quantity correspondence information such that the first physical quantity and the second physical quantity having the same elasticity in the biological tissue are converted to the same display form information.

10. A medical image display apparatus for displaying medical images of a biological tissue, said display apparatus comprising:

a physical quantity calculator configured to calculate a first physical quantity related to elasticity of the biological tissue;

a display image control unit configured to display a first elastic image having a display form corresponding to the first physical quantity calculated by the physical quantity calculator and a second elastic image having a display form corresponding to a second physical quantity related to elasticity of the biological tissue calculated by another medical image display apparatus as the medical images;

a storage unit configured to store second elasticity display data including second display form information corresponding to the second physical quantity and generated by the other medical image display apparatus;

a first elasticity display data generator configured to generate first elasticity display data including first display form information corresponding to the first physical quantity; and a second elasticity display data generator configured to convert the first display form information to the second display form information identical to the elasticity of the biological tissue represented by the first display form information to generate third elasticity display data based on display form correspondence information in which the first display form information is equal to the second display form information in the elasticity of the biological tissue, wherein the display image control unit is configured to display images in which portions having a same elasticity in the biological tissue in a same display form as the first and second elastic images, the first elastic image based on the third elasticity display data and the second elastic image based on the second elasticity display data.

11. The medical image display apparatus according to claim 10, wherein the display image control unit is configured to display an elastic image of the biological tissue based on the first elasticity display data.

12. The medical image display apparatus according to claim 10, wherein the display image control unit is configured to display a combined image of the first elastic image and the second elastic image.

13. The medical image display apparatus according to claim 10, further comprising:

an input unit configured to input a setting a measurement region at the first elastic image or the second elastic image; and a numerical display control unit configured to display a numeric value of the second physical quantity at the measurement region set at the input unit.

14. A medical image display apparatus for displaying medical images of a biological tissue, said display apparatus comprising:

a physical quantity calculator configured to calculate a first physical quantity related to elasticity of the biological tissue;

a display image control unit configured to display a first elastic image having a display form corresponding to the first physical quantity calculated by the physical quantity calculator and a second elastic image having a display form corresponding to a second physical quantity related to elasticity of the biological tissue calculated by another medical image display apparatus as the medical images;

a storage unit configured to store second elasticity display data including second display form information corresponding to the second physical quantity and generated by the other medical image display apparatus;

a first elasticity display data generator configured to generate first elasticity display data including first display form information corresponding to the first physical quantity; and a second elasticity display data generator configured to convert the second display form information to the first display form information identical to the elasticity of the biological tissue represented by the second display form information to generate third elasticity display data based on display form correspondence information in which the first display form information is equal to the second display form information in the elasticity of the biological tissue, wherein the display image control unit is configured to display images in which portions having a same elasticity in the biological tissue in a same display form as the first and second elastic images, the first elastic image based on the first elasticity display data and the second elastic image based on the third elasticity display data.

15. The medical image display apparatus according to claim 14, wherein the display image control unit is configured to display an elastic image of the biological tissue based on the second elasticity display data.

16. The medical image display apparatus according to claim 14, wherein the display image control unit is configured to display a combined image of the first elastic image and the second elastic image.

17. The medical image display apparatus according to claim 14, further comprising:

an input unit configured to input a setting a measurement region at the first elastic image or the second elastic image; and a numerical display control unit configured to display a numeric value of the second physical quantity at the measurement region set at the input unit.

* * * * *